United States Patent
Tang

(10) Patent No.: US 10,722,649 B2
(45) Date of Patent: *Jul. 28, 2020

(54) BLOCKCHAIN CONSENSUS NODE SELECTION

(71) Applicant: Alibaba Group Holding Limited, George Town (KY)

(72) Inventor: Qiang Tang, Hangzhou (CN)

(73) Assignee: Alibaba Group Holding Limited, George Town, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,356

(22) Filed: Dec. 20, 2019

(65) Prior Publication Data

US 2020/0129694 A1    Apr. 30, 2020

Related U.S. Application Data

(63) Continuation of application No. 16/042,897, filed on Jul. 23, 2018.

(30) Foreign Application Priority Data

Aug. 24, 2017 (CN) .......................... 2017 1 0736740

(51) Int. Cl.
*H04L 9/00* (2006.01)
*A61M 5/172* (2006.01)
(Continued)

(52) U.S. Cl.
CPC ............ *A61M 5/172* (2013.01); *A61M 5/142* (2013.01); *A61M 5/1407* (2013.01); *G06F 19/00* (2013.01);
(Continued)

(58) Field of Classification Search
CPC ............. G06F 16/2365; G06F 16/2379; H04L 2209/38; H04L 2209/463; H04L 2209/56;
(Continued)

(56) References Cited

U.S. PATENT DOCUMENTS 9,774,578 B1 *  9/2017  Ateniese ............... H04L 9/0894
9,998,286 B1 *  6/2018  Ramathal ............... G06Q 10/10
(Continued)

FOREIGN PATENT DOCUMENTS

CN    106445711    2/2017
CN    106603698    4/2017
(Continued)

OTHER PUBLICATIONS

Amir et al., "Prime: Byzantine Replication under Attack," IEEE Transactions of Dependable and Secure Computing, 2011, 8(4):564-577.
(Continued)

*Primary Examiner* — Gary S Gracia
(74) *Attorney, Agent, or Firm* — Fish & Richardson P.C.

(57) ABSTRACT

Techniques are described selecting consensus nodes in a blockchain. A voting process is performed by a plurality of shareholder nodes to generate a voting result for each shareholder node. The voting process comprises each shareholder node voting for a plurality of expected nodes, and the expected nodes and the plurality of shareholder nodes comprise a group of nodes associated with a blockchain. A shareholder node is a node that owns at least one share. A voting result is verified for each shareholder node. After the voting process, a number of shares owned by each node of the group of nodes id determined based on the voting result. A plurality of consensus nodes are selected from shareholder nodes based on the number of shares owned by each of the shareholder nodes.

17 Claims, 8 Drawing Sheets

(51) Int. Cl.
*G06Q 50/22* (2018.01)
*A61M 5/14* (2006.01)
*A61M 5/142* (2006.01)
*G06F 19/00* (2018.01)
*G16H 20/17* (2018.01)
*H04L 17/02* (2006.01)

(52) U.S. Cl.
CPC ......... *G06F 19/3468* (2013.01); *G06Q 50/22* (2013.01); *G16H 20/17* (2018.01); *A61M 2005/14208* (2013.01); *A61M 2205/52* (2013.01)

(58) Field of Classification Search
CPC . H04L 67/1097; H04L 9/0637; H04L 9/3236; H04L 9/3265
See application file for complete search history.

(56) References Cited

U.S. PATENT DOCUMENTS

| | | | | |
|---|---|---|---|---|
| 10,304,143 | B2* | 5/2019 | Kasper | G06Q 40/12 |
| 2015/0379510 | A1* | 12/2015 | Smith | G06Q 20/3829 705/71 |
| 2016/0164884 | A1 | 6/2016 | Sriram et al. | |
| 2017/0075877 | A1* | 3/2017 | Lepeltier | G06F 40/247 |
| 2017/0344987 | A1 | 11/2017 | Davis | |
| 2018/0101560 | A1* | 4/2018 | Christidis | G06F 16/215 |
| 2019/0068380 | A1 | 2/2019 | Tang | |
| 2019/0080392 | A1* | 3/2019 | Youb | H04L 9/0643 |

FOREIGN PATENT DOCUMENTS

| | | |
|---|---|---|
| CN | 106850536 | 6/2017 |
| CN | 106878071 | 6/2017 |

OTHER PUBLICATIONS

"bitshares.org [online],""Delegated Proof-of-Stake Consensus," "available on or before Jul. 5, 2017, via Internet Archive: Wayback Machine URL<Machine: https://web.archive.org/web/20170507054311/https://bitshares.org/technology/delegated-proof-of-stake-consensus/>, retrieved on Feb. 10, 2020, URL<https://bitshares.org/technology/delegated-proof-of-stake-consensus/>, 4 pages".

Crosby et al., "BlockChain Technology: Beyond Bitcoin," Sutardja Center for Entrepreneurship & Technology Technical Report, Oct. 16, 2015, 35 pages.

International Search Report and Written Opinion in International Application No. PCT/US2018/047975, dated Oct. 25, 2018, 13 pages.

Lerider [online], "Clarification on NEO, GAS and Consensus Nodes," Aug. 2017, [retrieved on Oct. 16, 2018], retrieved from: URL,https://medium.com/neo-smart-economy/clarification-on-neo-gas-and-consensus-nodes-aa94d4f4b09>, 5 pages.

Nakamoto, "Bitcoin: A Peer-to-Peer Electronic Cash System," www.bitcoin.org, 2005, 9 pages.

NEO Documentation [online], "Consensus," Jul. 2017, [retrieved on Oct. 10, 2018], retrieved from: URL<http://docs.neo.org/en-us/basic/consensus/consensus.html>, 9 pages.

NEO Documentation [online], "Election and Voting," Jul. 2017, [retrieved on Oct. 16, 2018], retrieved from: URL<http://docs.neo.org/en-us/node/gui/vote.html>, 6 pages.

PCT International Preliminary Report on Patentability in International application No. PCT/US2018/047975, dated Jul. 18, 2019, 6 pages.

Syta et al., "Scalable Bias-Resistant Distributed Randomness," International Association for Cryptologic Research, 2017, 1-17.

* cited by examiner

BLOCKCHAIN CONSENSUS NODE SELECTION

This application is a continuation of U.S. application Ser. No. 16/042,897, filed on Jul. 23, 2018, which claims priority to Chinese Patent Application No. 201710736740.5, filed on Aug. 24, 2017, which is hereby incorporated by reference in its entirety.

TECHNICAL FIELD

The present specification belongs to the field of computer data processing technologies, and in particular, to a consensus node selection process in the blockchain process.

BACKGROUND

Blockchain technology is generally a decentralized distributed database technology with characteristics such as decentralization, transparency, tamper-resistance, trust, etc. It can be used to record data information in a public or private peer-to-peer network. To ensure data consistency of a blockchain, data is generated and updated on the blockchain by using a consensus algorithm. The Practical Byzantine Fault Tolerance (PBFT) algorithm is a distributed consistency consensus algorithm commonly used in the industry.

Practical Byzantine Fault Tolerance (PBFT) is a state machine replication algorithm. Usually, some nodes are selected from a plurality of nodes on the blockchain as consensus nodes for consensus processing. Usually, there can be 4 to 11 consensus nodes participating in consensus. Currently, in PBFT, algorithms for consensus node selection mainly include random selection and fixed selection. In random consensus node selection, it is difficult to design an algorithm to make all nodes approve a newly selected consensus node, and node selection itself is a complicated consensus-reaching process. Fixed consensus node selection is simpler than random selection in terms of implementation, for example, only source code needs to be distributed to all nodes. However, this method becomes difficult when a fault occurs or when a consensus node is updated for some reason.

Currently, there is a need in the industry for a PBFT consensus node selection solution that is easy to implement and maintain, highly efficient, and reliable.

SUMMARY

One or more implementations of the present specification are intended to provide a consensus node selection method and apparatus, and server, to select a consensus node more easily, more efficiently, and more reliably in Practical Byzantine Fault Tolerance (PBFT).

The consensus node selection method and apparatus and the server provided in the one or more implementations of the present specification are implemented by using the following methods:

A consensus node selection method includes: obtaining an equity interest voting result of a shareholder node for at least one selected expected node, where the shareholder node includes a node that owns at least one of predetermined total equity rights; determining, based on the equity interest voting result, the number of shares owned by each shareholder node after equity interest voting; and determining a consensus node selection result based on the number of shares owned by each shareholder node after equity interest voting.

A consensus node selection apparatus includes: a voting result acquisition module, configured to obtain an equity interest voting result of a shareholder node for at least one selected expected node, where the at least one shareholder node includes a node that owns at least one of predetermined total shares; a voting result determining module, configured to determine, based on the equity interest voting result, the number of shares owned by each shareholder node after equity interest voting; and a consensus node determining module, configured to determine a consensus node selection result based on the number of shares owned by each shareholder node after equity interest voting.

A consensus node selection apparatus includes a processor and a memory configured to store a processor executable instruction. The processor executes the instruction to: obtain an equity interest voting result of a shareholder node for at least one expected node, where the shareholder node includes a node that owns at least one of predetermined total shares; determine, based on the equity interest voting result, the number of shares owned by each shareholder node after equity interest voting; and determine a consensus node selection result based on the number of shares owned by each shareholder node after equity interest voting.

A server includes at least one processor and a memory configured to store a processor executable instruction. The processor executes the instruction to: obtain an equity interest voting result of a shareholder node for at least one expected node, where the shareholder node includes a node that owns at least one of predetermined total shares; determine, based on the equity interest voting result, the number of shares owned by each shareholder node after equity interest voting; and determine a consensus node selection result based on the number of shares owned by each shareholder node after equity interest voting.

In the consensus node selection method and apparatus, and the server provided in one or more implementations of the present specification, a shareholder node can conduct equity interest voting, and select a node to participate in consensus based on the number of shares owned by shareholder nodes in a voting result. The method is easy to implement. A selection result is real and valid, and the voting result is disclosed in the whole network and can be approved by other nodes. Based on the implementation solution in the present specification, a consensus node can be quickly selected based on a share ratio after equity interest voting. As such, consumption in a consensus process is reduced, consensus processing steps are simplified, consensus node selection efficiency is improved, and a selection result is more reliable.

BRIEF DESCRIPTION OF DRAWINGS

To describe technical solutions in implementations of the present specification or in the existing technology more clearly, the following briefly describes the accompanying drawings for describing the implementations or the existing technology. Apparently, the accompanying drawings in the following descriptions merely show some implementations of the present specification, and a person of ordinary skill in the art can still derive other drawings from these accompanying drawings without creative efforts.

DESCRIPTION OF IMPLEMENTATIONS

Figure 1:
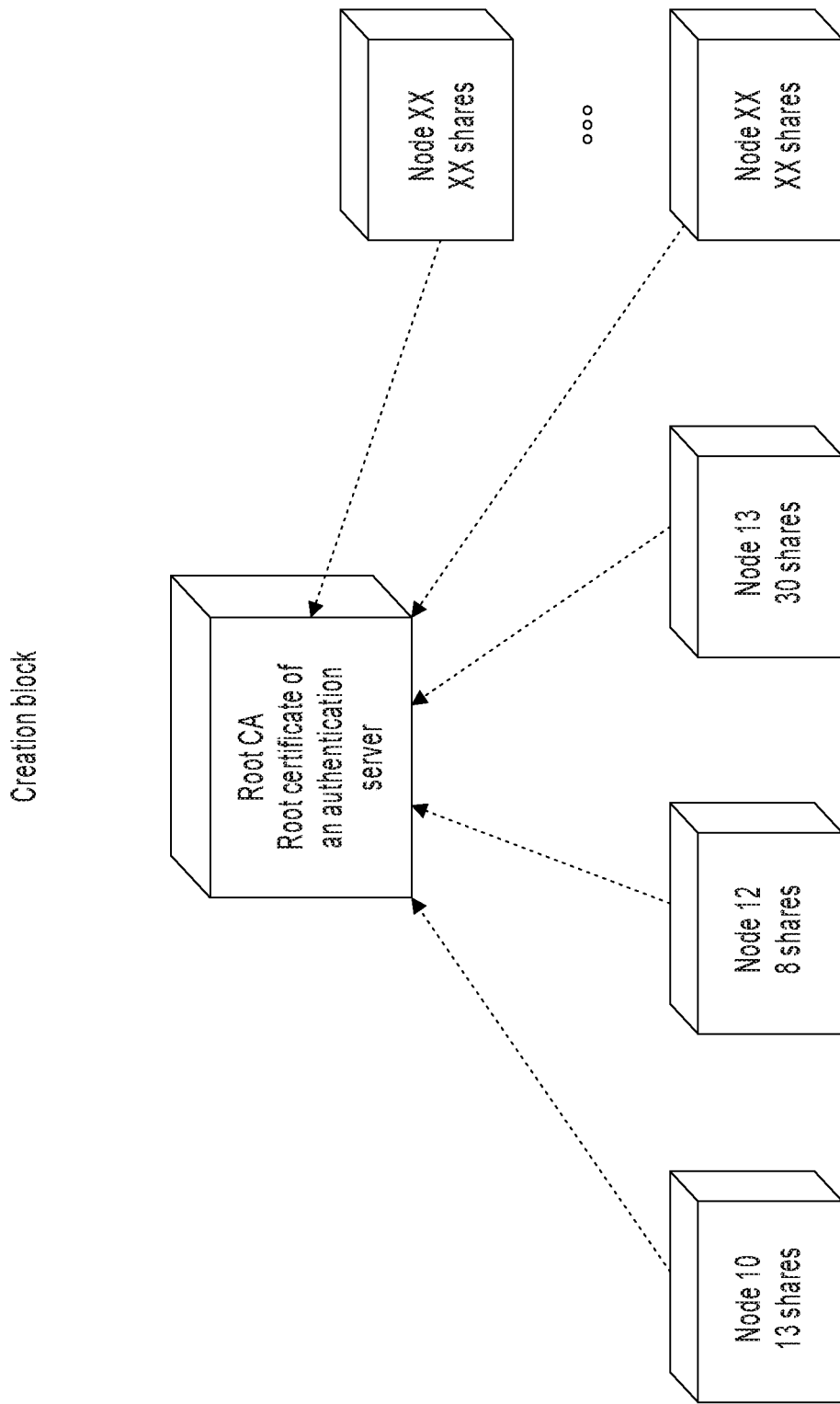
FIG. 1 is a schematic structural diagram illustrating allocation of predetermined total shares to nodes and blockchain nodes served by a certificate server, according to an implementation of the present specification.

To make a person skilled in the art better understand the technical solutions in the present specification, the following clearly and comprehensively describes the technical solutions in the implementations of the present specification with reference to the accompanying drawings in the implementations of the present specification. Apparently, the described implementations are merely some rather than all of the implementations of the present specification. Other implementations obtained by a person of ordinary skill in the art based on the implementations of the present specification without creative efforts shall fall within the protection scope of the present specification.

Although the present specification provides operational steps of the method or a structure of an apparatus in the following implementations or accompanying drawings, the method or the apparatus can include, based on conventional or non-creative effort, more operation steps or module units, or fewer operational steps or module units after combination of some operational steps or module units. In steps or structures without necessary logical causality, the execution sequence of the steps or the module structure of the apparatus is not limited to the execution sequence or the module structure shown in the implementations or the accompanying drawings in the present specification. When the method or the module structure is applied to an actual apparatus, server, or terminal product, the method or the module structure can be executed in a sequence based on the method or module structure shown in the implementations or the accompanying drawings, or can be executed in parallel (for example, in an environment of processing in parallel, in a multithreaded processing environment, and even in a distributed processing environment and a server cluster environment).

Practical Byzantine Fault Tolerance (PBFT) is a state-machine replication algorithm, that is, a service used as a state machine for modeling. The service is usually a specific application service provided by a server. For example, to complete a transfer, the service "transfer" can be modeled as a state machine. The state machine is replicated on different nodes in a distributed system. Generally, each copy of the state machine stores a service status, and implements a service operation. When the number of nodes on a blockchain exceeds a certain number, the nodes participating in consensus can lower the consensus efficiency. Therefore, some nodes need to be selected from the nodes on the blockchain as consensus nodes by using a method, to participate in consensus. For example, copies are generated through modeling, and other nodes are only synchronized with a consensus result (for example, are replicated) and do not participate in the consensus process.

In the PBFT consensus algorithm, usually, there are 4 to 11 nodes participating in consensus. If there are less than four nodes participating in consensus, the PBFT algorithm becomes invalid. If there are more than 11 nodes participating in consensus, consensus performance decreases with the increase of nodes. To balance Byzantine fault tolerance and the consensus performance, some nodes need to be selected as consensus nodes from a large number of nodes to participate in consensus. The consensus usually indicates that distributed nodes on a blockchain can use the same algorithm and the same data format (or the same processing protocol) to generate and update data, and this process can be implemented using different languages. The implementations of the present specification provide an effective PBFT consensus node selection method based on equity interest voting. The method is easy to implement. Selected nodes are real and valid, and can be approved by other nodes. In a specific implementation, a certificate server can be introduced, and a public key of the certificate server can be written into a creation block on a blockchain (a data storage block on the blockchain). Each node on the blockchain needs to apply for a root certificate to a root certificate server. The root certificate can be used to prove validity of a node identity.

In the present implementation, the total number of shares can be predetermined. For example, the total number of shares of all nodes on a blockchain can be set to 100. In the present implementation of the present specification, shares can have equal power (or weight), and the shares can be transferred from one node to another node on the blockchain. The shares can be considered as an asset and can be transacted on the blockchain. Validity of the shares can be proved in a transaction confirm process based on information recorded on a creation block. The total number of shares can be determined based on the actual number of nodes, an implementation environment, etc. Generally, the determined total number of shares is unique and remains unchanged. Certainly, in other implementations of the present specification, the total number of shares can be increased or decreased based on a service processing requirement, for example, a newly accessed important node owns 10 shares itself. The total shares can be allocated to corresponding nodes based on a service rule. A specific allocation rule can be determined based on a node size, a traffic volume, importance, etc. In one or more implementations of the present specification, a node allocated with a share of the predetermined total shares can be referred to as a shareholder node, or can be understood as a node that owns at least one of the predetermined total shares. FIG. 1 is a schematic structural diagram illustrating allocation of predetermined total shares to nodes and blockchain nodes served by a certificate server, according to the present specification.

Figure 2:
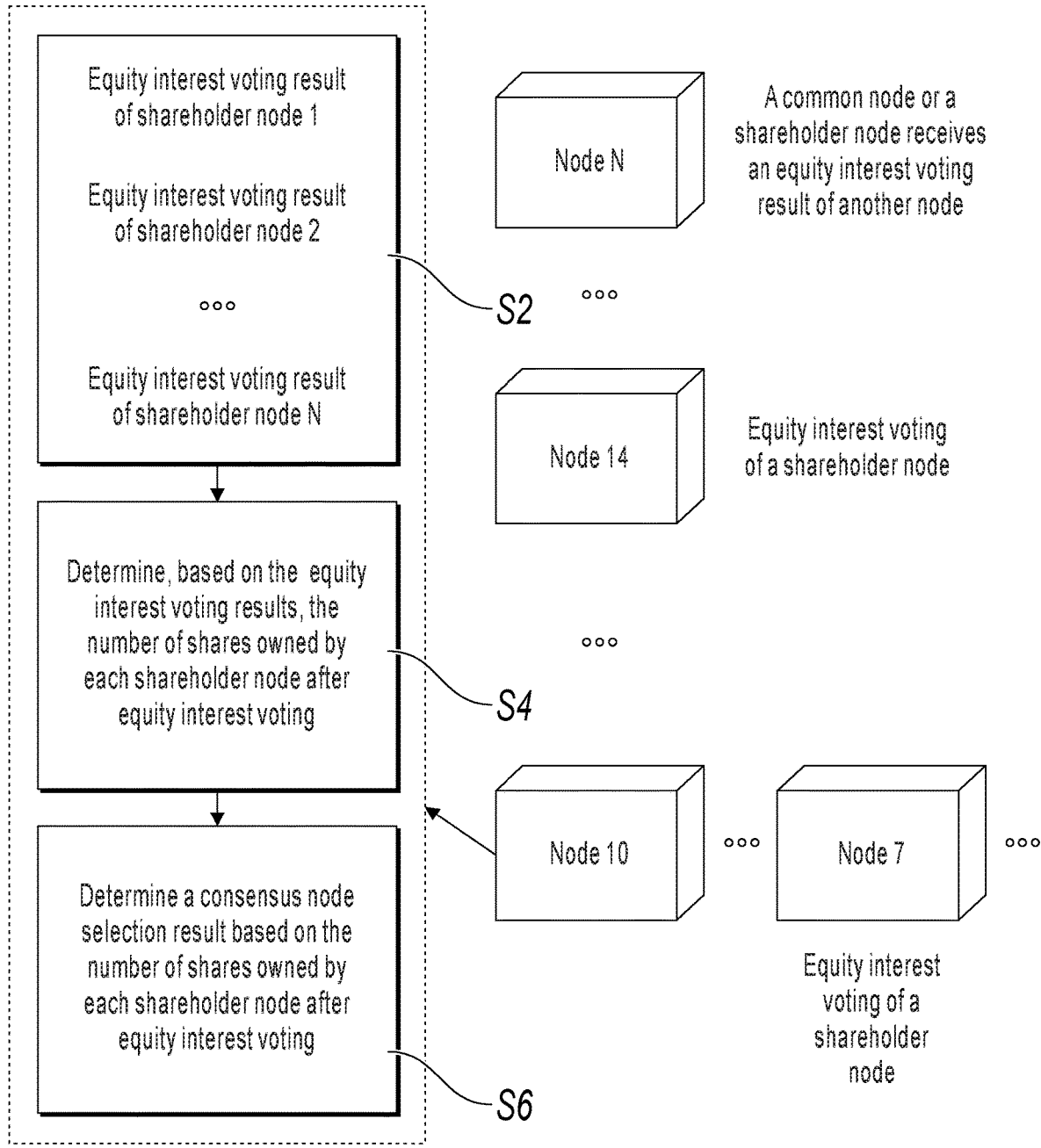
FIG. 2 is a schematic diagram illustrating a processing process of a method in an implementation scenario, according to the present specification.

Therefore, when a consensus node needs to be selected in PBFT, a node that owns a share can choose to vote for an expected node, and a voting result can be broadcasted to the entire blockchain network. After the voting, each node can receive the same equity interest voting result, and then determine a consensus node selection result based on the number of shares owned by each node. A specific implementation is shown in FIG. 2. The present specification provides an implementation of a consensus node selection method. The method can include the following steps:

S2. Obtain an equity interest voting result of a shareholder node for at least one expected node, where the shareholder node includes a node that owns at least one of predetermined total shares.

A node that the shareholder node votes for can be referred to as the expected node. The expected node can include a shareholder node that owns a share, or can include a node that owns no share before the voting. In an implementation, a node that owns a share can independently choose to vote for whichever node. The basis for selecting the expected node can include, but is not limited to, node service performance stability, a node service capacity, a selection policy determined by an operator, etc. In an implementation of the present specification, the selected expected node can include: at least one node selected by the shareholder node based on a predetermined consensus node selection condition to vote a share for.

The predetermined consensus node selection condition can include at least one of the node service performance stability, the node service capacity, the selection policy determined by an operator, etc. The shareholder node can vote for itself, or can vote for another node.

In the present implementation of the present specification, a node that owns a share (a shareholder node) can vote, and a common node with no shares cannot vote.

In an implementation, the total number of votes of a shareholder node is no more than the number of voting shares owned by the shareholder node. The voting shares do not include shares that other shareholder nodes vote for during consensus node selection. Therefore, in another implementation of the method provided in the present specification, the number of times that the share is validly transferred between nodes on a blockchain through voting is set to 1 in a single consensus node selection process.

In the present implementation, a shareholder node can vote for itself, or can vote for another node. The shareholder node cannot transfer votes obtained from other shareholder nodes. In a single voting process for consensus node selection, each share can be used by the shareholder node to vote only once.

In a specific example, node 1 has 10 shares, and the 10 shares are voting shares. Node 1 votes six shares for node 2, and node 3 votes three shares for node 1. Although node 1 has seven shares at this time, because three of them are voted by another node for node 1 and are not voting shares, node 1 has four shares that can be used for equity interest voting. Node 1 can vote for itself, or can vote for another expected node.

In another implementation of the present specification, a digital signature can be put on a voting result of the equity interest voting of the shareholder node. As such, another node can be prevented from forging the voting result of the shareholder node. The digital signature can also be used as verification data of the voting result to prevent the shareholder node from denying the voting result of itself. As such, reliability and security of the equity interest voting result are greatly improved. In an implementation provided in the present specification, the equity interest voting result can be generated by a shareholder node using its private key to digitally sign an equity interest voting result of the expected nodes.

Correspondingly, after the obtaining an equity interest voting result, the method further includes:

S20. Verify the equity interest voting result by using a corresponding public key of the shareholder node.

Figure 3:
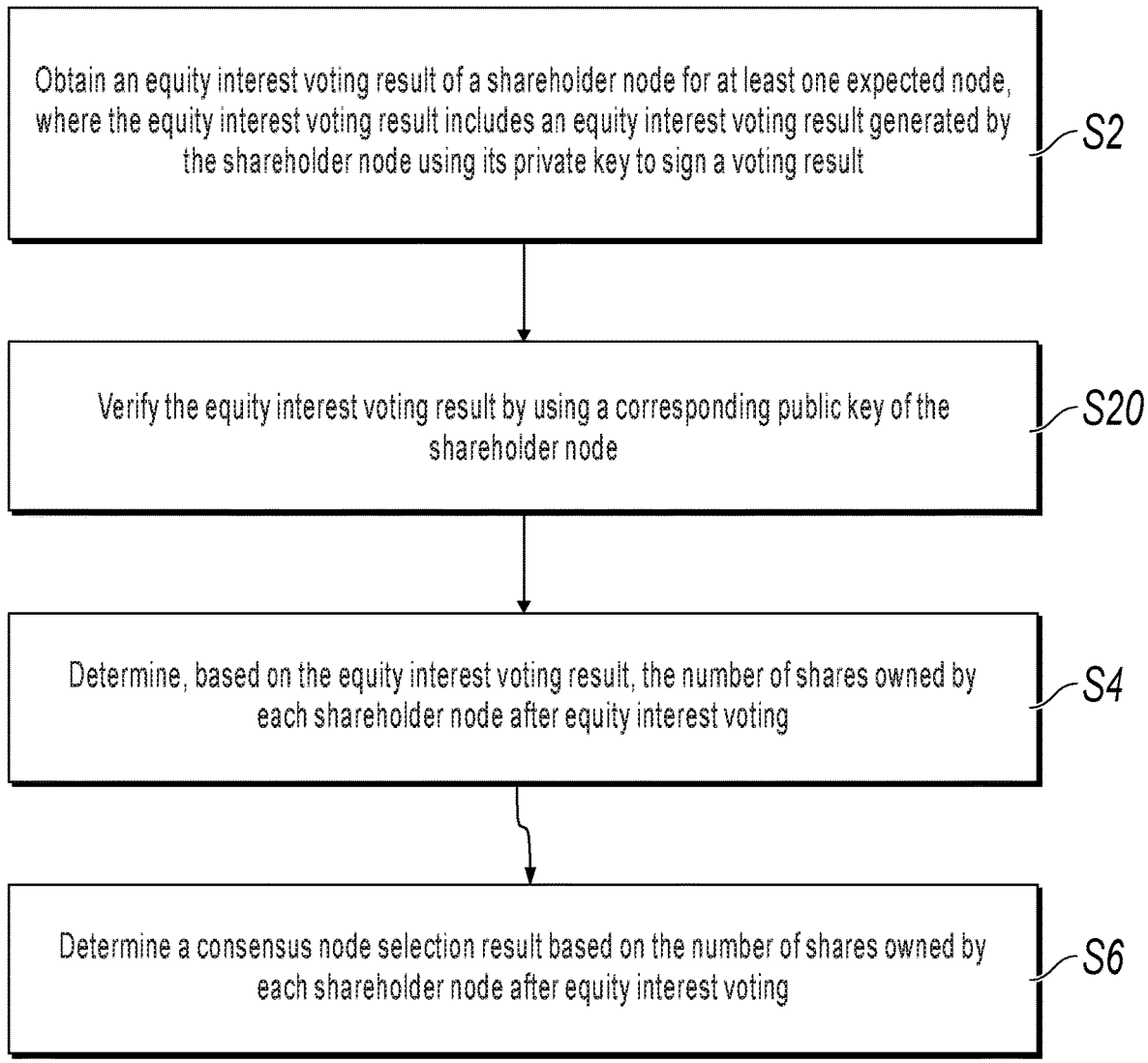
FIG. 3 is a schematic flowchart illustrating another implementation of the method, according to the present specification.

FIG. 3 is a schematic flowchart illustrating another implementation of the method, according to the present specification. In the present implementation, a private key in asymmetric encryption can be used to sign a signature on the voting result, and a corresponding public key can be broadcasted to other nodes. Correspondingly, the result with the signature signed by using the private key can be verified by using the public key of the corresponding node, to confirm whether the equity interest voting result and a sender of the equity interest voting result are valid (legal). If the equity interest voting result is invalid, an alarm can be sent or another predetermined processing operation can be performed.

S4. Determine, based on the equity interest voting result, the number of shares owned by each shareholder node after equity interest voting.

After the shareholder node votes, the equity interest voting result of the shareholder node can be broadcasted to all nodes on the blockchain. As such, each node on the blockchain can receive the equity interest voting result of the shareholder node, and the nodes can receive the same equity interest voting result. In the present implementation, after all shareholder nodes vote, a share allocation structure on the nodes usually changes. For example, if a node that originally owns shares has voted all the shares for another node while receiving no votes from other nodes, that node now has no share. That is, before the equity interest voting, the node was a shareholder node. But after the equity interest voting, the node has changed to a common node with no shares. If a common node with no shares before equity interest voting owns a share after equity interest voting, it becomes a new shareholder node.

Therefore, after equity interest voting, a shareholder node or a common node can determine, based on a received equity interest voting result or an equity interest voting result of itself, the number of shares owned by each shareholder node. In the implementation scenario of the present implementation, after equity interest voting, the sum of shares of all shareholder nodes remains unchanged before and after equity interest voting.

In a specific example, before equity interest voting, shareholder node 10 owns 20 shares, shareholder node 11 owns 25 shares, shareholder node 15 owns 30 shares, shareholder node 8 owns 10 shares, and shareholder node 6 owns 15 shares. After equity interest voting, all the nodes receive the same equity interest voting result. An equity interest voting result received by shareholder node 10 can be as follows: shareholder node 10 owns 9 shares, shareholder node 11 owns 20 shares, shareholder node 15 owns 35 shares, shareholder node 8 owns 3 shares, shareholder node 6 owns 20 shares, and shareholder node 7 owns 13 shares. After equity interest voting, not only the numbers of shares owned by the original shareholder nodes has changed, but also a new shareholder node 7 appears and owns 13 shares.

S6. Determine a consensus node selection result based on the number of shares owned by each shareholder node after equity interest voting.

After the equity interest voting result is obtained, the consensus node selection result can be determined based on the number of shares owned by each current shareholder node. The specific number of selected consensus nodes and a selection method can be set based on an actual application scenario or a processing requirement. For example, the five shareholder nodes that own the most shares are selected as the consensus nodes.

In another implementation scenario of the method provided in the present specification, there can be nodes that own the same number of shares after equity interest voting. For example, node 10 and node 11 each own 20 shares. However, due to limitations on the number of consensus nodes (for example, five consensus nodes need to be selected, four consensus nodes have been determined, and each determined consensus node owns more than 20 shares), one of node 10 and node 11 needs to be selected as a consensus node. In an implementation provided in the present specification, when there are nodes that own the same number of shares, the consensus nodes can be selected based on a time sequence of generating node root certificates. In another implementation, the determining a consensus node selection result based on the number of shares owned by each shareholder node after equity interest voting can include the following step:

S601. If the shareholder nodes include nodes that own the same number of shares after equity interest voting, select a consensus node from the nodes that own the same number of shares based on a time sequence of generating node root certificates, where the node root certificate includes data information used to prove a node identity and applied to a specified certificate server by a node on a blockchain.

As described above, in an implementation method, before being added to the blockchain, a node on the blockchain needs to apply to the designated certificate server for a root certificate that is used to prove the node is valid. The earlier a node is added to the blockchain, the earlier a root certificate of the node is generated. Generally, the earlier a node is added to the blockchain, the more stable, optimal, and reliable of its running parameters, server performance, data processing policy, etc. Therefore, in the present implementation, when there are nodes that own the same number of shares, a node with an earlier generated root certificate can be preferentially selected as a consensus node. In a specific example, when the root certificates are numbered by using information including the time of generating the root certificates, the consensus nodes can be selected in ascending order of numbers of the root certificates.

Figure 4:
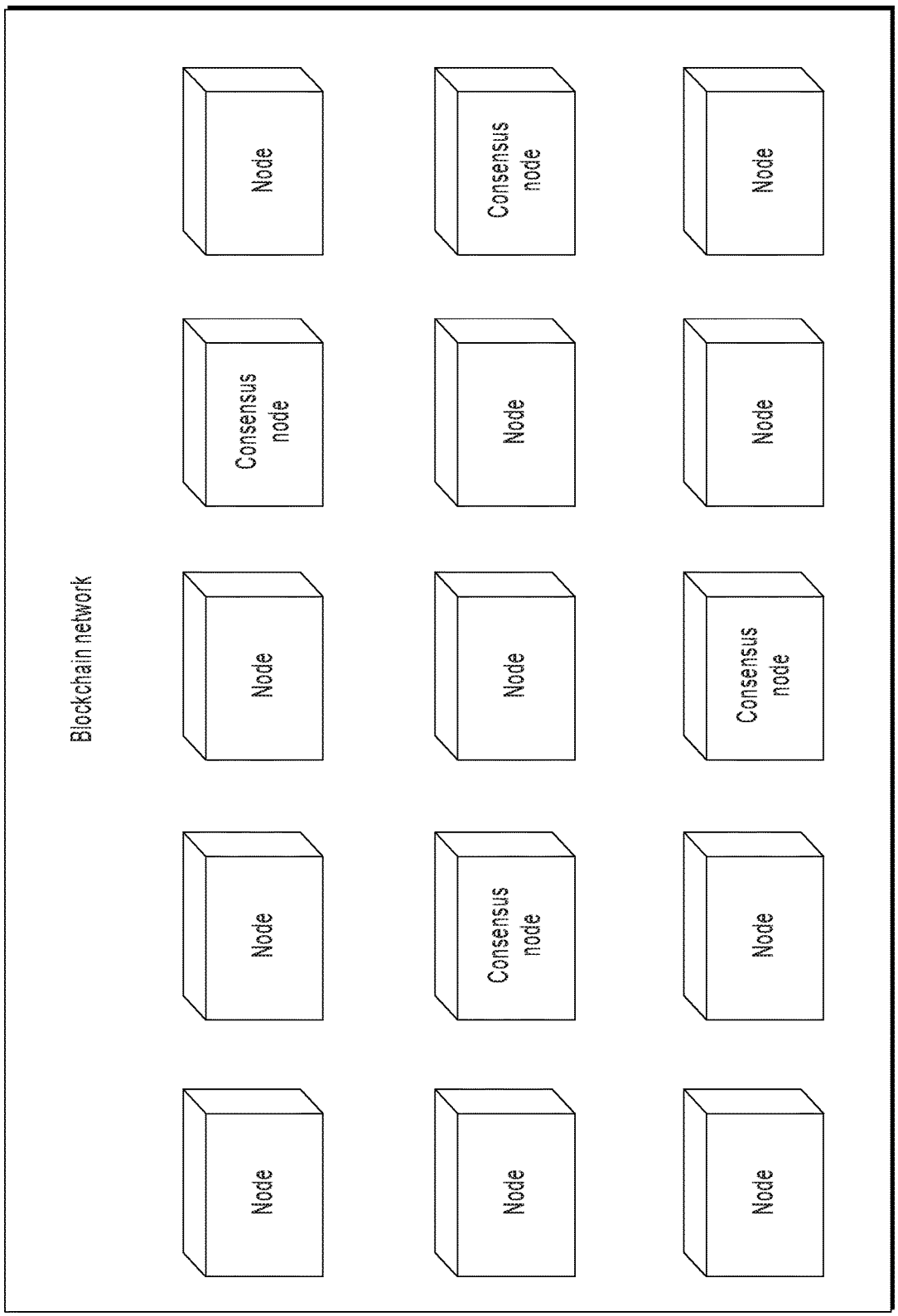
FIG. 4 is a schematic diagram illustrating a scenario of selecting a consensus node in a blockchain network, according to an implementation of the present specification.

FIG. 4 is a schematic diagram illustrating a scenario of selecting a consensus node in a blockchain network, according to an implementation of the present specification. One or more implementations of the present specification provide a consensus node selection method. A shareholder node can conduct equity interest voting, and select a node to participate in consensus based on the number of shares owned by shareholder nodes in a voting result. The method is easy to implement. A selection result is real and valid, and the voting result is disclosed in the whole network and can be approved by other nodes. Based on the implementation solution in the present specification, a consensus node can be quickly selected based on a share ratio after equity interest voting. As such, consumption in a consensus process is reduced, consensus processing steps are simplified, consensus node selection efficiency is improved, and a selection result is more reliable.

Based on the previous consensus node selection method, the present specification further provides a consensus node selection apparatus. The apparatus can include an apparatus using a system (including a distributed system), software (application), a module, a component, a server, a client, a quantum computer, etc. in the method in one or more implementations of the present specification and including necessary implementation hardware. Based on the same inventive concept, an apparatus provided in the one or more implementations of the present specification is described in the following implementations. An implementation solution of the apparatus for resolving a problem is similar to the implementation solution of the method. Therefore, for one or more specific implementations of the apparatus in the present specification, refer to the implementation of the previous method. Details are not described here again. In the following, the term "unit" or "module" can implement a combination of software and/or hardware of a predetermined function. Although the apparatus described in the following implementations is preferably implemented by using software, the apparatus can also be implemented by using hardware or a combination of software and hardware.

Figure 5:
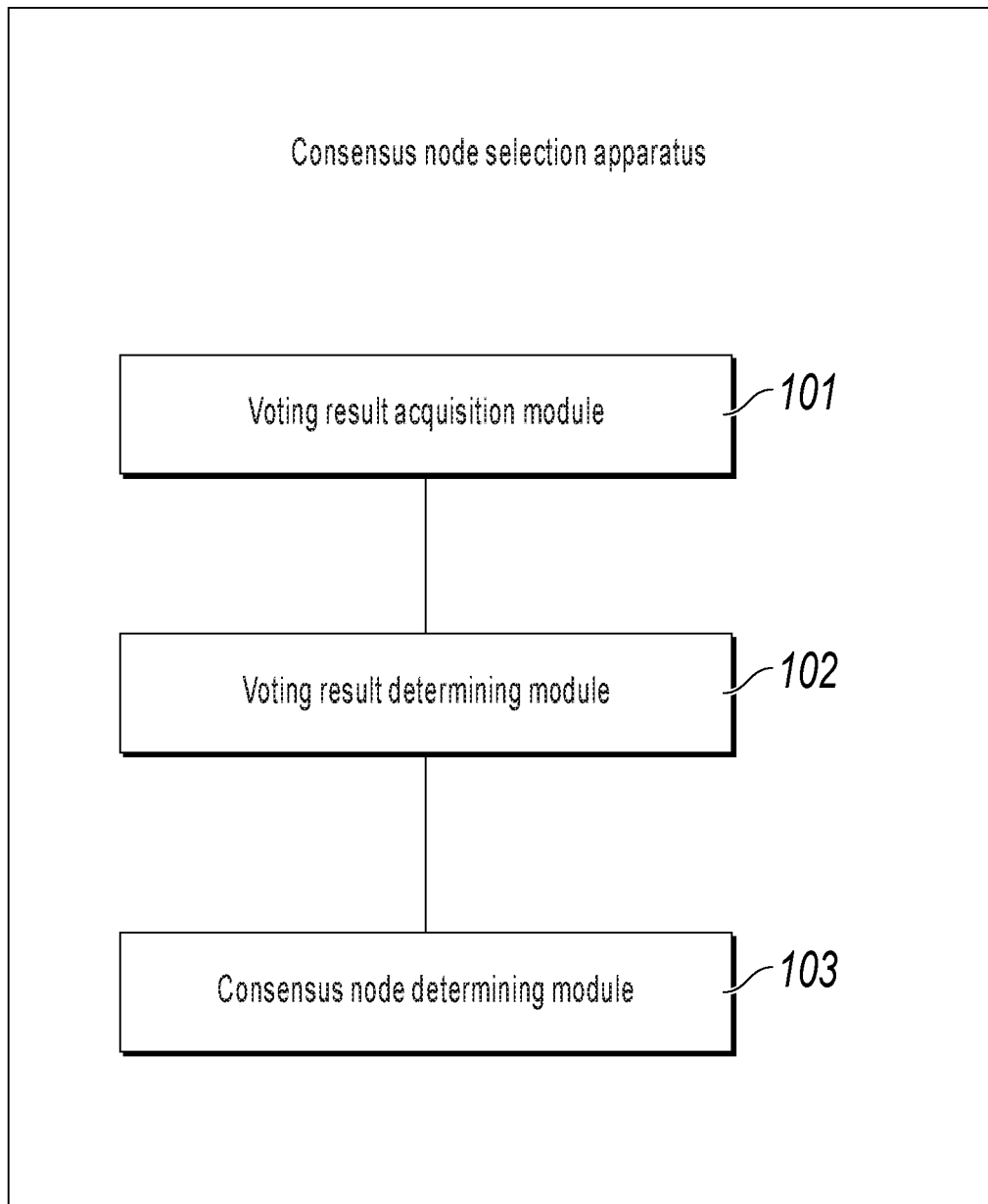
FIG. 5 is a schematic structural diagram illustrating modules in a consensus node selection apparatus, according to an implementation of the present specification.

FIG. 5 is a schematic structural diagram illustrating modules in a consensus node selection apparatus, according to an implementation of the present specification. As shown in FIG. 5, the apparatus can include: a voting result acquisition module 101, configured to obtain an equity interest voting result of a shareholder node for at least one expected node, where the shareholder node includes a node that owns at least one of predetermined total shares; a voting result determining module 102, configured to determine, based on the equity interest voting result, the number of shares owned by each shareholder node after equity interest voting; and a consensus node determining module 103, configured to determine a consensus node selection result based on the number of shares owned by each shareholder node after equity interest voting.

The total number of shares can be determined based on the actual number of nodes, an implementation environment, etc. Generally, the determined total number of shares is unique and remains unchanged. The total shares can be allocated to corresponding nodes based on a service rule. A specific allocation rule can be determined based on a node size, traffic volume, importance, etc.

When a consensus node needs to be selected in PBFT, a node that owns a share can choose to vote for an expected node, and a voting result can be broadcasted to the entire blockchain network. After the voting, the nodes can receive the same equity interest voting result, and then determine a consensus node selection result based on the number of shares owned by each node. Based on the implementation solution of the apparatus in the present specification, the consensus node can be quickly selected based on a share ratio after equity interest voting. As such, consumption in a consensus process is reduced, consensus processing steps are simplified, consensus node selection efficiency is improved, and a selection result is more reliable.

In another implementation of the apparatus provided in the present specification, if the shareholder nodes include nodes that own the same number of shares after equity interest voting, the consensus node determining module 103 selects a consensus node from the nodes that own the same number of shares based on a time sequence of generating node root certificates. The node root certificate includes data information used to prove a node identity and applied for by a node on a blockchain to a specified certificate server.

Figure 6:
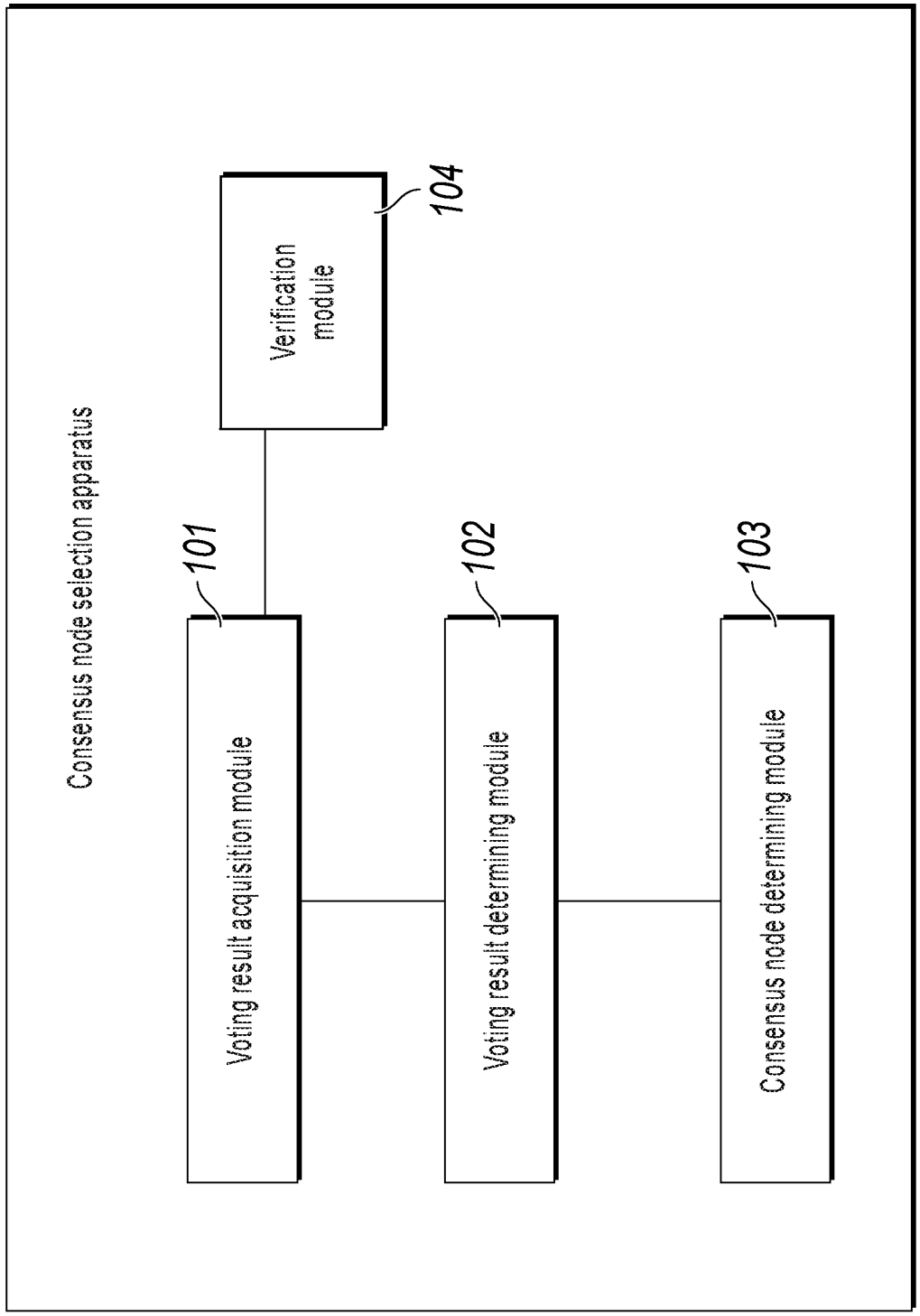
FIG. 6 is a schematic structural diagram illustrating modules in a consensus node selection apparatus, according to another implementation of the present specification.

FIG. 6 is a schematic structural diagram illustrating modules in a consensus node selection apparatus, according to another implementation of the present specification. As shown in FIG. 6, in an implementation of the apparatus provided by the present specification, the equity interest voting result can include: an equity interest voting result generated after the shareholder node signs a signature on a voting result generated after equity interest voting for the expected node, by using a private key of the shareholder node.

Correspondingly, the apparatus can further include: a verification module 104, configured to verify the equity interest voting result by using a corresponding public key of the shareholder node after the equity interest voting result is obtained.

In an implementation, a node that owns a share can independently choose to vote for which node. The basis for selecting the expected node can include, but is not limited to, node service performance stability, a node service capacity, a selection policy determined by an operator, etc. In another implementation of the apparatus provided in the present specification, the selected expected node can include at least one node selected by the shareholder node based on a predetermined consensus node selection condition to vote a share for.

In an implementation, the total number of votes of a shareholder node can be set as no more than the number of voting shares owned by the shareholder node. The voting shares do not include shares that other shareholder nodes vote for the shareholder node during consensus node selection. Therefore, in another implementation of the apparatus, the number of times that the share is validly transferred between nodes on a blockchain through voting is set to 1 in a single consensus node selection process.

In this implementation, in a single voting process for consensus node selection, each share can be used by the shareholder node to vote only once, and the shareholder node cannot transfer votes obtained from other shareholder nodes.

The apparatus in the previous implementation can be implemented on a single node, and can include a common node or the shareholder node. Because the voting result is broadcast to all nodes in the blockchain network, and all the nodes receive the same equity interest voting result, each node can confirm the consensus node selection result based on the equity interest voting result.

It is worthwhile to note that the descriptions of the previous apparatus in the present specification can further include another implementation based on descriptions of related method implementation. The implementations in the present specification are all described in a progressive manner. Mutual reference can be made for the same or similar parts in the implementations. Each implementation focuses on a difference from other implementations. A module apparatus implementation is similar to a method implementation, and therefore is described briefly. For related parts, refer to partial descriptions in the method implementation.

Specific implementations of the present specification are described above. Other implementations fall within the scope of the appended claims. In some situations, the actions or the steps recorded in the claims can be performed in an order different from the order in the implementations and can still achieve a desired result. In addition, the process described in the accompanying drawings does not necessarily require the shown order or sequence to achieve the desired result. In some implementations, multitask processing and parallel processing are also be feasible or possibly advantageous.

The present specification provides the consensus node selection apparatus. A shareholder node can conduct equity interest voting, and select a node to participate in consensus based on the number of shares owned by shareholder nodes in a voting result. The method is easy to implement. A selection result is real and valid, and the voting result is disclosed to the whole network and can be approved by other nodes. Based on the implementation solution in the present specification, a consensus node can be quickly selected based on a share ratio after equity interest voting. As such, consumption in a consensus process is reduced, consensus processing steps are simplified, consensus node selection efficiency is improved, and a selection result is more reliable.

The consensus node selection method provided in the present specification can be implemented by a processor executing a corresponding program instruction in a computer. For example, it can be implemented at a PC end by using the C++ language in a Windows operating system, or implemented by using a corresponding program design language in another system such as Linux, Android, iOS, or implemented based on processing logic of a quantum computer. In an implementation of the apparatus for consensus node selection in the present specification, the apparatus can include a processor and a memory configured to store a processor executable instruction. The processor executes the instruction to: obtain an equity interest voting result of a shareholder node for at least one expected node, where the shareholder node includes a node that owns at least one of predetermined total shares; determine, based on the equity interest voting result, the number of shares owned by each shareholder node after equity interest voting; and determine a consensus node selection result based on the number of shares owned by each shareholder node after equity interest voting.

It is worthwhile to note that the descriptions of the previous apparatus in the present specification can further include another implementation based on descriptions of related method implementations. The implementations in the present specification are all described in a progressive manner. Mutual reference can be made for the same or similar parts in the implementations. Each implementation focuses on a difference from other implementations. A hardware+program implementation is similar to a method implementation, and therefore is described briefly. For related parts, refer to partial descriptions in the method implementation.

The previous apparatus or method can be used for a server of a blockchain service system to select or confirm a consensus node in a blockchain network. A processing server for consensus node selection can quickly select a consensus node based on a share ratio after equity interest voting. As such, consumption in a consensus process is reduced, consensus processing steps are simplified, consensus node selection efficiency is improved, and a selection result is more reliable. The server can include a terminal apparatus using a system (including a distributed system), software (application), a module, a component, a server, a client, a quantum computer, etc. in one or more method implementations or apparatus implementations in the present specification and including necessary implementation hardware.

Figure 7:
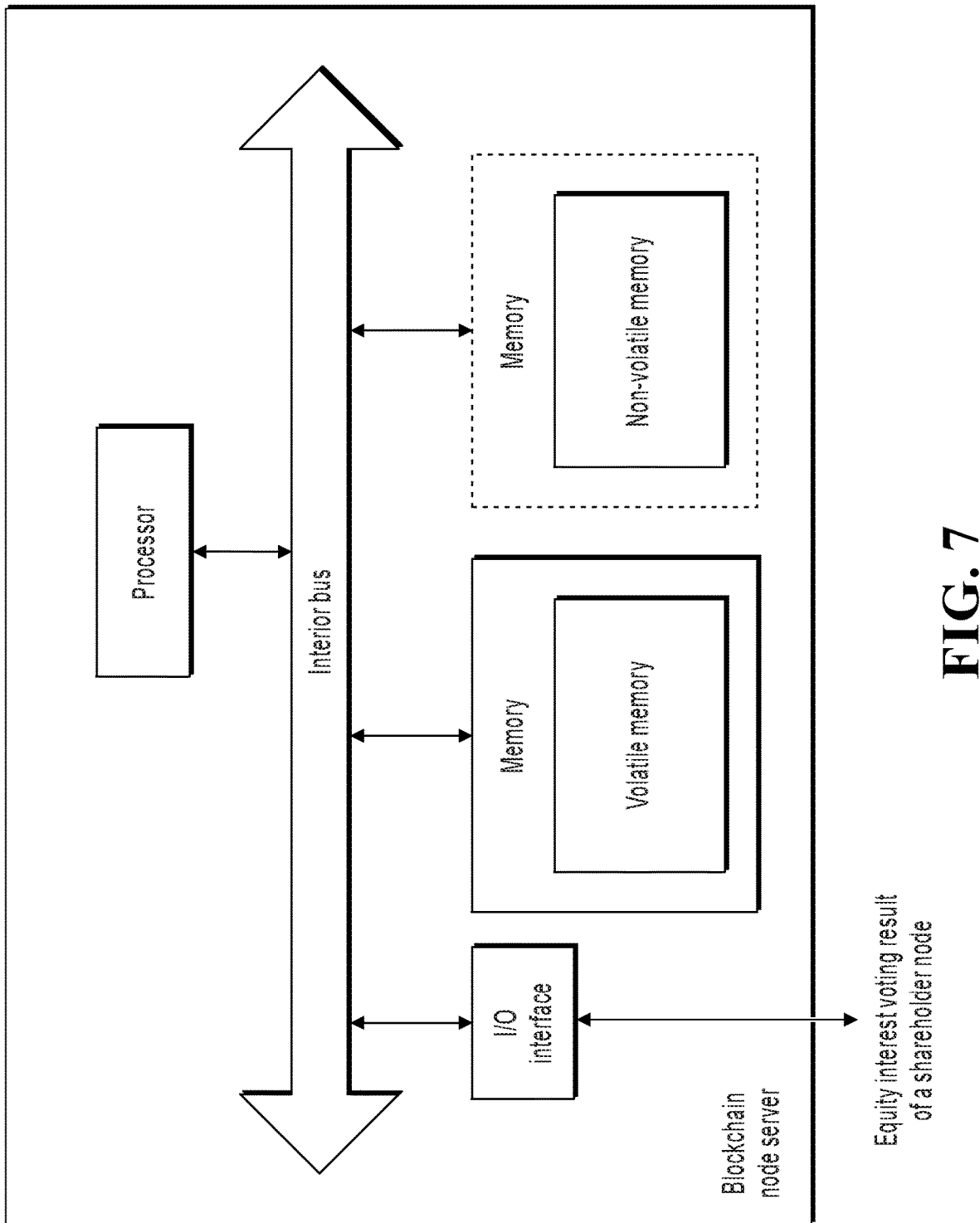
FIG. 7 is a schematic structural diagram illustrating a server, according to an implementation of the present specification.

FIG. 7 is a schematic structural diagram illustrating a server, according to an implementation of the present specification. The server can include at least one processor and a memory configured to store a processor executable instruction. The processor executes the instruction to: obtain an equity interest voting result of a shareholder node for at least one expected node, where the shareholder node includes a node that owns at least one of predetermined total shares; determine, based on the equity interest voting result, the number of shares owned by each shareholder node after equity interest voting; and determine a consensus node selection result based on the number of shares owned by each shareholder node after equity interest voting.

It is worthwhile to note that the hardware+program apparatus or server can further include another implementation based on the descriptions in the method implementation. For a specific implementation, reference can be made to the corresponding descriptions in the method implementation. Details are not described here again.

In the consensus node selection method and apparatus and the server provided in one or more implementations of the present specification, a shareholder node can conduct equity interest voting, and select a node to participate in consensus based on the number of shares owned by shareholder nodes in a voting result. The method is easy to implement. A selection result is real and valid, and the voting result is disclosed in the whole network and can be approved by other nodes. Based on the implementation solution in the present specification, a consensus node can be quickly selected based on a share ratio after equity interest voting. As such, consumption in a consensus process is reduced, consensus processing steps are simplified, consensus node selection efficiency is improved, and a selection result is more reliable.

Although content of the present specification provides descriptions about data setting, acquisition, interaction, calculation, determining, etc. for the basis for selecting an expected node by a shareholder node, limitations on the number of times that a share is validly transferred during voting, using a private key to encrypt and a public key to decrypt a voting result, determining a consensus node based on the number of shares owned by nodes after voting, etc., the present specification is not necessarily limited to cases that conform to an industry communications standard, standard blockchain data storage, and computer processing and storage rules, or the cases described in one or more implementations of the present specification. An implementation solution obtained after making slight modification based on some industry standards, or by using a self-defined method, or based on implementation described in the implementations can also achieve an implementation effect that is the same as, equivalent to, or similar to the previous implementations or that can be predicted after transformation. An implementation using a data acquisition, storage, determining, and processing method obtained after such modification or transformation is still within the scope of one or more optional implementation solutions of the present specification.

In the 1990s, improvement of a technology can be clearly distinguished between hardware improvement (for example, improvement of circuit structures such as a diode, a transistor, and a switch) and software improvement (improvement of a method procedure). However, with the development of technologies, improvement of many method procedures can be considered as a direct improvement of a hardware circuit structure. Designers almost all program an improved method procedure to a hardware circuit, to obtain a corresponding hardware circuit structure. Therefore, it cannot be said that an improvement of a method procedure cannot be implemented by using a hardware entity module. For example, a programmable logic device (PLD) (for example, a field programmable gate array (FPGA)) is a type of an integrated circuit. A logical function of the programmable logic device is determined by component programming executed by a user. The designers perform programming to "integrate" a digital system into a single PLD without requiring a chip manufacturer to design and produce a dedicated integrated circuit chip. In addition, instead of manually producing an integrated circuit chip, the programming is mostly implemented by "logic compiler" software, which is similar to a software compiler used during program development. Original code before compiling is also written in a specified programming language, which is referred to as hardware description language (HDL). There is more than one type of HDL, such as an Advanced Boolean Expression Language (ABEL), an Altera Hardware Description Language (AHDL), Confluence, a Cornell University Programming Language (CUPL), an HDCal, a Java Hardware Description Language (JHDL), a Lava, a Lola, a MyHDL, a PALASM, and a Ruby Hardware Description Language (RHDL). Currently, the very-high-speed Integrated Circuit Hardware Description Language (VHDL) and Verilog are most commonly used. A person skilled in the art should also understand that a method procedure only needs to be logically programmed, and programmed to the integrated circuit by using the previous hardware description languages, so that a hardware circuit that implements the logical method procedure can be easily obtained.

The controller can be implemented in any suitable manner. For example, the controller can be a microprocessor, a processor, a computer-readable medium, a logic gate, a switch, an application-specific integrated circuit (ASIC), a programmable logic controller, or an embedded microprocessor that stores computer-readable program code (such as software or firmware) that can be executed by the microprocessor or the processor. Examples of the controller include but are not limited to the following microcontrollers: ARC 625D, Atmel AT91SAM, Microchip PIC18F26K20, and Silicone Labs C8051F320. The memory controller can also be implemented as a part of the control logic of the memory. A person skilled in the art also knows that a controller can be implemented in a manner of computer-readable program code only, and the steps in the method can be logically programmed to enable the controller to further implement same functions in forms of a logical gate, a switch, an application-specific integrated circuit, a programmable logic controller, an embedded microcontroller, etc. Therefore, the controller can be considered as a hardware component, and an apparatus included in the controller and configured to implement various functions can also be considered as a structure in the hardware component. Alternatively, an apparatus configured to implement various functions can be considered as both a software module for implementing the method and a structure in the hardware component.

The system, the apparatus, the module, or the unit described in the foregoing implementations can be implemented by a computer chip or an entity, or implemented by a product with a specified function. A typical implementation device is a computer. The computer can be, for example, a personal computer, a laptop computer, an in-vehicle human-machine interaction device, a cellular phone, a camera phone, a smartphone, a personal digital assistant, a media player, a navigation device, an email device, a game console, a tablet computer, a wearable device, or a combination of any of these devices.

Although the present specification provides the operational steps of the method in an implementation or a flowchart, more or fewer operational steps can be included based on the conventional or non-creative means. The sequence of steps enumerated in the implementations is merely one of a plurality of step execution sequences, and does not represent a unique execution sequence. In practice, when an apparatus or a terminal product executes steps, the execution can be performed in a sequence shown in an implementation or a method shown in the accompanying drawing, or performed in parallel (for example, in an environment of processing in parallel, in a multithreaded processing environment, and even in a distributed data processing environment). The terms "comprise", "include", or their any other variants are intended to cover a non-exclusive inclusion, so that a process, a method, an article, or a device that includes a list of elements not only includes those elements, but also includes other elements which are not expressly listed, or further includes elements inherent to such process, method, article, or device. When there are no more restrictions, it is also possible that there is another same or equivalent element in the process, the method, a product, or a device that includes the element.

For ease of description, the foregoing apparatus is described by dividing the functions into various modules. Certainly, when implementing the present specification, a function of each module can be implemented in one or more pieces of software and/or hardware, or a module that implements the same function can be implemented as a combination of a plurality of submodules or subunits. The described apparatus implementation is merely an example. For example, the unit division is merely logical function division and can be other division in actual implementation. For example, a plurality of units or components can be combined or integrated into another system, or some features can be ignored or not performed. In addition, the displayed or discussed mutual couplings or direct couplings or communication connections can be implemented by using some interfaces. The indirect couplings or communication connections between the apparatuses or units can be implemented in electronic, mechanical, or other forms.

A person skilled in the art also knows that a controller can be implemented in a manner of computer-readable program code only, and the steps in the method can be logically programmed to enable the controller to further implement same functions in forms of a logical gate, a switch, an application-specific integrated circuit, a programmable logic controller, an embedded microcontroller, etc. Therefore, the controller can be considered as a hardware component, and an apparatus included in the controller and configured to implement various functions can also be considered as a structure in the hardware component. Alternatively, an apparatus configured to implement various functions can be considered as both a software module for implementing the method and a structure in the hardware component.

The present disclosure is described with reference to the flowcharts and/or block diagrams of the method, the device (system), and the computer program product according to the implementations of the present disclosure. It should be understood that computer program instructions can be used to implement each process and/or each block in the flowcharts and/or the block diagrams and a combination of a process and/or a block in the flowcharts and/or the block diagrams. These computer program instructions can be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more procedures in the flowcharts and/or in one or more blocks in the block diagrams.

These computer program instructions can be stored in a computer-readable memory that can instruct the computer or any other programmable data processing devices to work in a specific manner, so that the instructions stored in the computer-readable memory can generate an artifact that includes an instruction apparatus. The instruction apparatus implements a specific function in one or more procedures in the flowcharts and/or in one or more blocks in the block diagrams.

These computer program instructions can be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more procedures in the flowcharts and/or in one or more blocks in the block diagrams.

In a typical configuration, the computing device includes one or more processors (CPU), an input/output interface, a network interface, and a memory.

The memory can include a non-persistent memory, a random access memory (RAM), a non-volatile memory, and/or another form that are in a computer-readable medium, for example, a read-only memory (ROM) or a flash memory (flash memory). The memory is an example of the computer-readable medium.

The computer-readable medium includes persistent, non-persistent, movable, and unmovable media that can implement information storage by using any method or technology. Information can be a computer-readable instruction, a data structure, a program module, or other data. An example of a computer storage medium includes, but is not limited to a phase change memory (PRAM), a static random access memory (SRAM), a dynamic random access memory (DRAM), another type of random access memory (RAM), a read-only memory (ROM), an electrically erasable programmable read-only memory (EEPROM), a flash memory or another memory technology, a compact disc read-only memory (CD-ROM), a digital versatile disc (DVD) or other optical storage, a cassette magnetic tape, tape and disk storage or another magnetic storage device or any other non-transmission media that can be configured to store information that a computing device can access. As defined in the present specification, the computer-readable medium does not include transitory computer-readable media (transitory media), such as a modulated data signal and a carrier.

A person skilled in the art should understand that the implementations of the present specification can be provided as a method, a system, or a computer program product. Therefore, the present specification can use a form of hardware only implementations, software only implementations, or implementations with a combination of software and hardware. In addition, the present specification can use a form of a computer program product implemented on one or more computer-usable storage media (including but not limited to a disk memory, a CD-ROM, an optical memory, etc.) including computer-usable program code.

The present specification can be described in the general context of computer executable instructions executed by a computer, such as a program unit. Generally, the program module includes a routine, a program, an object, a component, a data structure, etc. for executing a particular task or implementing a particular abstract data type. The present specification can also be practiced in distributed computing environments in which tasks are executed by remote processing devices connected by using a communications network. In the distributed computing environments, program modules can be located in both local and remote computer storage media including storage devices.

The implementations in the present specification are all described in a progressive manner. Mutual reference can be made for the same or similar parts in the implementations. Each implementation focuses on a difference from other implementations. A system implementation is similar to a method implementation, and therefore is described briefly; and for the relevant parts, reference can be made to partial descriptions of the method implementation. In the descriptions of the present specification, reference terms such as "an implementation", "some implementations", "example", "specific example", and "some examples" mean that specific features, structures, materials, or features described with reference to the implementations or examples are included in at least one implementation or example in the present specification. In the present specification, the foregoing terms are described not necessarily for the same implementation or example. In addition, the described specific features, structures, materials, or characteristics can be combined in a proper manner in any one or more implementations or examples. Further, a person skilled in the art can combine different embodiments or examples descried in the present specification and features of different implementations or examples without mutual contradiction.

The foregoing descriptions are merely one or more implementations of the present specification, and are not intended to limit the present specification. For a person skilled in the art, the present specification can have various changes and variations. Any modifications, equivalent substitutions, and improvements made within the spirit and the principle of the present specification shall fall within the scope of the claims in the present specification.

Figure 8:
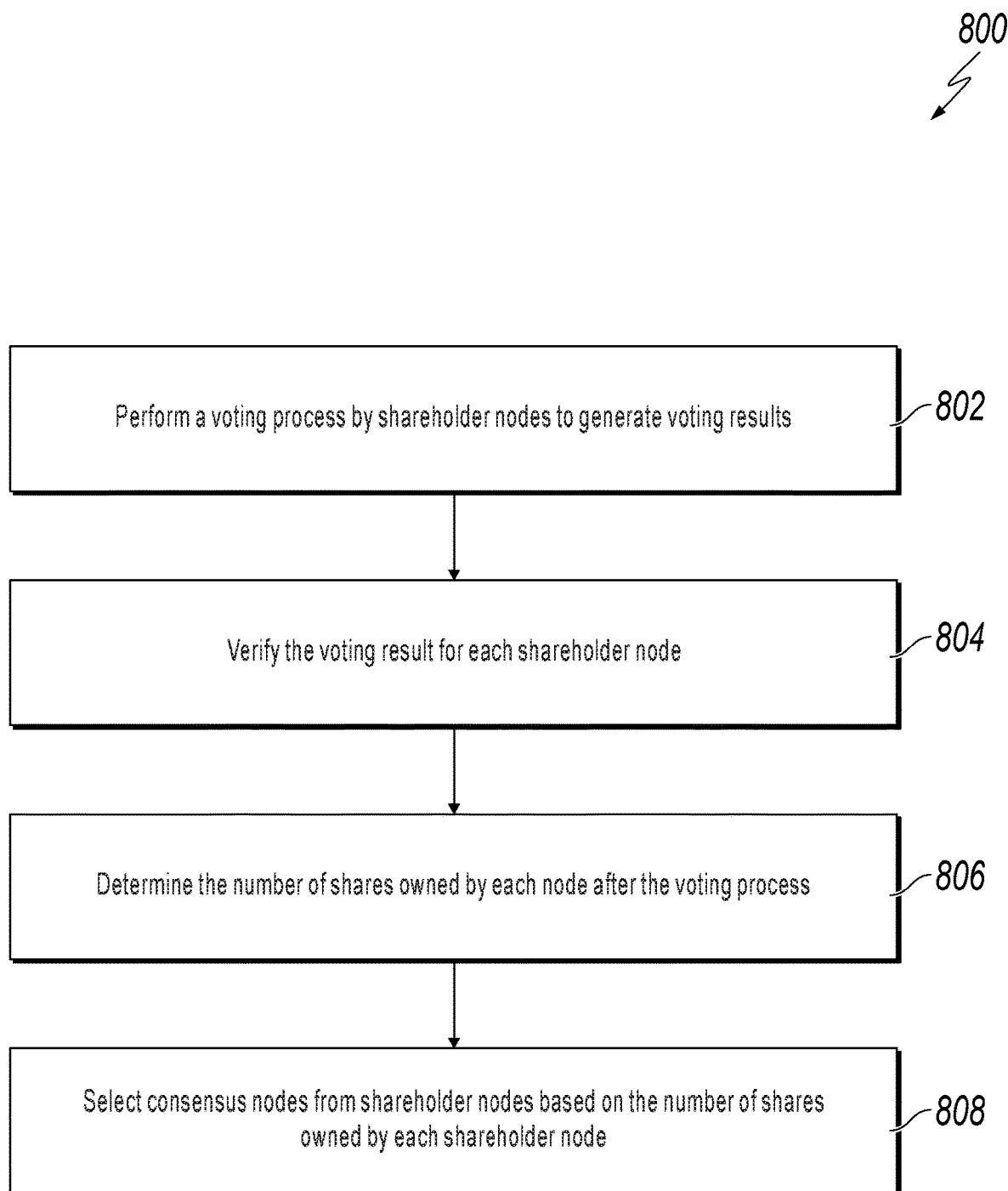
FIG. 8 is a flowchart illustrating an example of a computer-implemented method for selecting consensus nodes in a blockchain, according to an implementation of the present disclosure.

FIG. 8 is a flowchart illustrating an example of a computer-implemented method 800 for selecting consensus nodes in a blockchain, according to an implementation of the present disclosure. For clarity of presentation, the description that follows generally describes method 800 in the context of the other figures in this description. However, it will be understood that method 800 can be performed, for example, by any system, environment, software, and hardware, or a combination of systems, environments, software, and hardware, as appropriate. In some implementations, various steps of method 800 can be run in parallel, in combination, in loops, or in any order.

At 802, a voting process is performed by a plurality of shareholder nodes to generate a voting result for each shareholder node. The voting process includes the shareholder nodes voting for a plurality of selected expected nodes. The expected nodes and the shareholder nodes belong to a group of nodes associated with a blockchain. A shareholder node is a node that owns at least one share. In some implementations, a node allocated with a share of the predetermined total shares can be referred to as a shareholder node. A node that the shareholder nodes vote for can be referred to as an expected node. The expected node can be a shareholder node that owns a share before the voting, or can be a node that owns no share before the voting. In some implementations, a shareholder node can independently choose for which expected nodes to vote. In some implementations, the basis for selecting the expected node can include, but is not limited to, node service performance stability, a node service capacity, or a selection policy determined by an operator.

In some implementations, only shareholder nodes can vote, and common nodes that own no shares are unable to vote. The shareholder nodes can vote for themselves, or for other nodes. However, the shareholder nodes cannot transfer shares they receive from another node. That is, during each voting process, a share can only be used to vote once. For example, before the voting process, shareholder node 1 has ten shares, and node 1 votes six of the ten shares to node 2, whereas another shareholder node 3 votes three shares to node 1. Although node one now has seven shares (10−6+3=4), it can only use four shares to vote because the other three shares were transferred from another node. From 802, method 800 proceeds to 804.

At 804, a voting result (for example, an equity interest voting result) for each shareholder node is verified. In some implementations, the voting result for each shareholder node can be verified by a digital signature, preventing the voting result from being forged, and preventing the shareholder nodes from denying their voting results. In some implementations, a shareholder node can digitally sign its voting result for the expected nodes by using a private key associated with the shareholder node. In some implementations, a private key using asymmetric encryption can be used to sign a signature on the voting result. A corresponding public key can be broadcast to nodes in the blockchain.

The voting result with the signature can be verified by another node in the blockchain using the broadcast public key. The verification can be used to confirm whether the voting result and a sender of the voting result are valid (legal). If the equity interest voting result is invalid, an alarm can be sent or another predetermined processing operation can be performed. From 804, method 800 proceeds to 806.

At 806, a number of shares owned by each node (that is, an equity interest) of the group of nodes after the voting process is determined based on the voting result. In some implementations, after the shareholder node votes, the voting result of that shareholder node can be broadcast to all nodes in the blockchain. As such, each node in the blockchain can receive the voting result of the shareholder node.

In some implementations, after the voting process, a shareholder node or a common node can determine, based on the received broadcasted voting result, or based on the voting result on its own node, the number of shares owned by each shareholder node. After the voting process, not only the number of shares owned by the original shareholder nodes has changed, but also a new shareholder node. From 806, method 800 proceeds to 808.

At 808, a plurality of consensus nodes are selected from shareholder nodes based on the number of shares owned by each of the shareholder nodes. The shareholder nodes are nodes own at least one share after the voting process. In some implementations, when the number of nodes on a blockchain exceeds a certain number, the nodes participating in consensus can lower the consensus efficiency. Therefore, some nodes need to be selected from the nodes on the blockchain as consensus nodes by using a method, to participate in consensus. For example, in the PBFT consensus algorithm, usually, to balance Byzantine fault tolerance and the consensus performance, some nodes need to be selected as consensus nodes from a large number of nodes to participate in consensus. The consensus usually indicates that distributed nodes on a blockchain can use the same algorithm and the same data format (or the same processing protocol) to generate and update data, and this process can be implemented using different languages.

In the present implementation, after all shareholder nodes vote, a share allocation structure on the nodes usually changes. For example, if a node that originally owns shares has voted all the shares for another node while receiving no votes from other nodes, that node now has no share. That is, before the equity interest voting, the node was a shareholder node. But after the equity interest voting, the node has changed to a common node with no shares. If a common node with no shares before voting owns a share after equity interest voting, it becomes a new shareholder node.

After the equity interest voting result is obtained, the consensus node selection result can be determined based on the number of shares owned by each shareholder node. The specific number of selected consensus nodes and a selection method can be set based on an actual application scenario or a processing requirement. For example, the five shareholder nodes that own the most shares are selected as the consensus nodes.

In some implementations, before being added to the blockchain, a node on the blockchain (both shareholder and common nodes) needs to apply to a designated certificate server for a root certificate that is used to prove the node is valid. The earlier a node is added to the blockchain, the earlier a root certificate of the node is generated.

In some implementations, if the shareholder nodes include nodes that own the same number of share after the voting process and there is a limitation on the number of consensus nodes, the selection of consensus nodes from the shareholder nodes that own the same number of shares can be based on a time sequence of generating node root certificates. The earlier a node is added to the blockchain, the more stable, optimal, and reliable the node's running parameters, server performance, or data processing policy are considered to be. Therefore, in the present implementation, when there are nodes that own the same number of shares, a node with an earlier generated root certificate can be preferentially selected as a consensus node. In a specific example, when the root certificates are numbered by using information including the time of generating the root certificates, the consensus nodes can be selected in ascending order of numbers of the root certificates. After 808, the method 800 stops.

Implementations of the present application can solve technical problems in blockchain consensus node selection. Blockchain technology is generally a decentralized distributed database technology with characteristics such as decentralization, transparency, tamper-resistance, and trust. It can be used to record data information in a public or private peer-to-peer network. To ensure data consistency of a blockchain, data is generated and updated on the blockchain by using a consensus algorithm. The PBFT algorithm is a distributed consistency consensus algorithm commonly used in the industry. In PBFT, conventional algorithms for consensus node selection mainly include random selection and fixed selection. However, under conventional approaches, it is difficult to design an algorithm to make all nodes approve a newly selected consensus node after a complicated consensus node selecting process. Moreover, although fixed consensus node selection is simpler than a random selection in terms of implementation, the method becomes difficult when a fault occurs or when a consensus node is updated for some reason. What is needed is a technique to bypass these problems in the conventional methods, and providing a PBFT consensus node selection solution that is easy to implement and maintain, highly-efficient, and reliable.

Implementations of the present application describe methods and apparatus for improving consensus node selection in a blockchain. During the consensus node selecting process, shareholder nodes can vote for expected nodes to generate voting results. The voting results can be verified by the shareholder nodes by digitally signing the results using a private key, and the corresponding public key will be broadcast to all the nodes in the blockchain. In this way, all the nodes can receive the voting results and approve the result simultaneously, resulting in a simpler and quicker way for nodes within the blockchain to approve a newly selected consensus node. Moreover, because of a signed digital signature, the voting results cannot be forged or be denied by shareholder nodes, improving data security. The consensus nodes can be selected based on the number of shares owned by each node, and when there are nodes having the same number of shares, the selection can be based on a time sequence. Generally, the earlier a node is added to the blockchain indicates the more stable, optimal, and reliable a node's running parameters, server performance, or data processing policy is. Therefore, selecting consensus nodes located at an earlier time sequence within the blockchain can result in more stable and reliable nodes participating in blockchain decision-making processes.

The method is also easy to implement. The voting result is disclosed to the entire network and can be approved by other nodes. Based on the described solution, a consensus node can be quickly selected based on a share ratio after voting. As such, consumption in a consensus process is reduced, consensus processing steps are simplified, consensus node selection efficiency is improved, and a selection result is more reliable.

Embodiments and the operations described in this specification can be implemented in digital electronic circuitry, or in computer software, firmware, or hardware, including the structures disclosed in this specification or in combinations of one or more of them. The operations can be implemented as operations performed by a data processing apparatus on data stored on one or more computer-readable storage devices or received from other sources. A data processing apparatus, computer, or computing device may encompass apparatus, devices, and machines for processing data, including by way of example a programmable processor, a computer, a system on a chip, or multiple ones, or combinations, of the foregoing. The apparatus can include special purpose logic circuitry, for example, a central processing unit (CPU), a field programmable gate array (FPGA) or an application-specific integrated circuit (ASIC). The apparatus can also include code that creates an execution environment for the computer program in question, for example, code that constitutes processor firmware, a protocol stack, a database management system, an operating system (for example an operating system or a combination of operating systems), a cross-platform runtime environment, a virtual machine, or a combination of one or more of them. The apparatus and execution environment can realize various different computing model infrastructures, such as web services, distributed computing and grid computing infrastructures.

A computer program (also known, for example, as a program, software, software application, software module, software unit, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be executed on one computer or on multiple computers that are located at one site or distributed across multiple sites and interconnected by a communication network.

Processors for execution of a computer program include, by way of example, both general- and special-purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data. A computer can be embedded in another device, for example, a mobile device, a personal digital assistant (PDA), a game console, a Global Positioning System (GPS) receiver, or a portable storage device. Devices suitable for storing computer program instructions and data include non-volatile memory, media and memory devices, including, by way of example, semiconductor memory devices, magnetic disks, and magneto-optical disks. The processor and the memory can be supplemented by, or incorporated in, special-purpose logic circuitry.

Mobile devices can include handsets, user equipment (UE), mobile telephones (for example, smartphones), tablets, wearable devices (for example, smart watches and smart eyeglasses), implanted devices within the human body (for example, biosensors, cochlear implants), or other types of mobile devices. The mobile devices can communicate wirelessly (for example, using radio frequency (RF) signals) to various communication networks (described below). The mobile devices can include sensors for determining characteristics of the mobile device's current environment. The sensors can include cameras, microphones, proximity sensors, GPS sensors, motion sensors, accelerometers, ambient light sensors, moisture sensors, gyroscopes, compasses, barometers, fingerprint sensors, facial recognition systems, RF sensors (for example, Wi-Fi and cellular radios), thermal sensors, or other types of sensors. For example, the cameras can include a forward- or rear-facing camera with movable or fixed lenses, a flash, an image sensor, and an image processor. The camera can be a megapixel camera capable of capturing details for facial and/or iris recognition. The camera along with a data processor and authentication information stored in memory or accessed remotely can form a facial recognition system. The facial recognition system or one-or-more sensors, for example, microphones, motion sensors, accelerometers, GPS sensors, or RF sensors, can be used for user authentication.

To provide for interaction with a user, embodiments can be implemented on a computer having a display device and an input device, for example, a liquid crystal display (LCD) or organic light-emitting diode (OLED)/virtual-reality (VR)/augmented-reality (AR) display for displaying information to the user and a touchscreen, keyboard, and a pointing device by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments can be implemented using computing devices interconnected by any form or medium of wireline or wireless digital data communication (or combination thereof), for example, a communication network. Examples of interconnected devices are a client and a server generally remote from each other that typically interact through a communication network. A client, for example, a mobile device, can carry out transactions itself, with a server, or through a server, for example, performing buy, sell, pay, give, send, or loan transactions, or authorizing the same. Such transactions may be in real time such that an action and a response are temporally proximate; for example an individual perceives the action and the response occurring substantially simultaneously, the time difference for a response following the individual's action is less than 1 millisecond (ms) or less than 1 second (s), or the response is without intentional delay taking into account processing limitations of the system.

Examples of communication networks include a local area network (LAN), a radio access network (RAN), a metropolitan area network (MAN), and a wide area network (WAN). The communication network can include all or a portion of the Internet, another communication network, or a combination of communication networks. Information can be transmitted on the communication network according to various protocols and standards, including Long Term Evolution (LTE), 5G, IEEE 802, Internet Protocol (IP), or other protocols or combinations of protocols. The communication network can transmit voice, video, biometric, or authentication data, or other information between the connected computing devices.

Features described as separate implementations may be implemented, in combination, in a single implementation, while features described as a single implementation may be implemented in multiple implementations, separately, or in any suitable sub-combination. Operations described and claimed in a particular order should not be understood as requiring that the particular order, nor that all illustrated operations must be performed (some operations can be optional). As appropriate, multitasking or parallel-processing (or a combination of multitasking and parallel-processing) can be performed.

What is claimed is:

1. A computer-implemented method executed by central processing unit, comprising:
   when a number of distributed nodes on a blockchain exceeds a certain number, distributed nodes participate in a consensus node selection process using a Practical Byzantine Fault Tolerance (PBFT) algorithm including:
   performing an equity interest voting process by a plurality of shareholder nodes to generate a voting result for each shareholder node, wherein the voting process comprises each shareholder node voting for a plurality of expected nodes where a share is used to vote, wherein an expected node is a node that a shareholder node votes for, wherein the expected nodes and the plurality of shareholder nodes comprise a group of nodes associated with a the blockchain; and wherein a shareholder node is a node that owns at least one share, wherein a share is an asset having equal power or weight and can be transacted on the blockchain. and the shares can be transferred from one node to another node on the blockchain;
   verifying a voting result for each shareholder node, wherein verifying the voting result for each shareholder node comprises:

signing, by the shareholder node, the voting result for the shareholder node using a private key of the shareholder node;
broadcasting a public key corresponding to the private key to nodes in the blockchain; and
verifying the voting result by using a corresponding public key of the shareholder node;
determining, after the voting process and based on the voting results, a number of shares owned by each node of the group of nodes and all the nodes can receive the voting result and approve the voting result simultaneously for nodes within the blockchain to approve a newly selected consensus node; and
selecting, a plurality of consensus nodes from shareholder nodes based on the number of shares owned by each of the shareholder nodes.

2. The method of claim 1, wherein an expected node is voted for by a shareholder node based on a predetermined consensus node selection condition.

3. The method of claim 1, wherein a number of times that the share can be validly transferred between nodes on a blockchain through the voting process is set to 1 in a single consensus node selection process.

4. The computer-implemented method of claim 1, wherein a specific number of shares used to select consensus nodes can be set based on an application scenario or a processing requirement.

5. The computer-implemented method of claim 1, wherein each node in the blockchain is associated with a root certificate.

6. The computer-implemented method of claim 5, wherein selecting a plurality of consensus nodes comprises selecting consensus nodes from a plurality of shareholder nodes that own the same number of shares based on a time sequence of a node root certificate generated for each shareholder node.

7. A non-transitory, computer-readable medium storing one or more instructions executable by a computer system to perform operations comprising:
when a number of distributed nodes on a blockchain exceeds a certain number, distributed nodes participate in a consensus node selection process using a Practical Byzantine Fault Tolerance (PBFT) algorithm including:
performing an equity interest voting process by a plurality of shareholder nodes to generate a voting result for each shareholder node, wherein the voting process comprises each shareholder node voting for a plurality of expected nodes where a share is used to vote, wherein an expected node is a node that a shareholder node votes for, wherein the expected nodes and the plurality of shareholder nodes comprise a group of nodes associated with a the blockchain; and wherein a shareholder node is a node that owns at least one share, wherein a share is an asset having equal power or weight and can be transacted on the blockchain, and the shares can be transferred from one node to another node on the blockchain;
verifying a voting result for each shareholder node, wherein verifying the voting result for each shareholder node comprises:
signing, by the shareholder node, the voting result for the shareholder node using a private key of the shareholder node;
broadcasting a public key corresponding to the private key to nodes in the blockchain; and
verifying the voting result by using a corresponding public key of the shareholder node;
determining, after the voting process and based on the voting results, a number of shares owned by each node of the group of nodes and all the nodes can receive the voting result and approve the voting result simultaneously for nodes within the blockchain to approve a newly selected consensus node; and
selecting, a plurality of consensus nodes from shareholder nodes based on the number of shares owned by each of the shareholder nodes.

8. The non-transitory, computer-readable medium of claim 7, wherein the an expected node is selected voted for by a shareholder node based on a predetermined consensus node selection condition.

9. The non-transitory, computer-readable medium of claim 7, wherein a number of times that the share can be validly transferred between nodes on a blockchain through the voting process is set to 1 in a single consensus node selection process.

10. The non-transitory, computer-readable medium of claim 7, wherein a specific number of shares used to select consensus nodes can be set based on an application scenario or a processing requirement.

11. The non-transitory, computer-readable medium of claim 7, wherein each node in the blockchain is associated with a root certificate.

12. The non-transitory, computer-readable medium of claim 11, wherein selecting a plurality of consensus nodes comprises selecting consensus nodes from a plurality of shareholder nodes that own the same number of shares based on a time sequence of a node root certificate generated for each shareholder node.

13. A computer-implemented system, comprising: one or more computers; and
one or more computer memory devices interoperably coupled with the one or more computers and having tangible, non-transitory, machine-readable media storing one or more instructions that, when executed by the one or more computers, perform one or more operations comprising:
when a number of distributed nodes on a blockchain exceeds a certain number, distributed nodes participate in a consensus node selection process using a Practical Byzantine Fault Tolerance (PBFT) algorithm including:
performing an equity interest voting process by a plurality of shareholder nodes to generate a voting result for each shareholder node, wherein the voting process comprises each shareholder node voting for a plurality of expected nodes where a share is used to vote, wherein an expected node is a node that a shareholder node votes for, wherein the expected nodes and the plurality of shareholder nodes comprise a group of nodes associated with a the blockchain; and wherein a shareholder node is a node that owns at least one share, wherein a share is an asset having equal power or weight and can be transacted on the blockchain. and the shares can be transferred from one node to another node on the blockchain;
verifying a voting result for each shareholder node, wherein verifying the voting result for each shareholder node comprises:
signing, by the shareholder node, the voting result for the shareholder node using a private key of the shareholder node;
broadcasting a public key corresponding to the private key to nodes in the blockchain; and verifying the voting result by using a corresponding public key of the shareholder node;

determining, after the voting process and based on the voting results, a number of shares owned by each node of the group of nodes and all the nodes can receive the voting result and approve the voting result simultaneously for nodes within the blockchain to approve a newly selected consensus node; and selecting, a plurality of consensus nodes from shareholder nodes based on the number of shares owned by each of the shareholder nodes.

14. The computer-implemented system of claim 13, wherein an expected node is selected voted for by a shareholder node based on a predetermined consensus node selection condition.

15. The computer-implemented system of claim 13, wherein a number of times that the share can be validly transferred between nodes on a blockchain through the voting process is set to 1 in a single consensus node selection process.

16. The computer-implemented system of claim 13, wherein a specific number of shares used to select consensus nodes can be set based on an application scenario or a processing requirement.

17. The computer-implemented system of claim 13, wherein each node in the blockchain is associated with a root certificate; and wherein selecting a plurality of consensus nodes comprises selecting consensus nodes from a plurality of shareholder nodes that own the same number of shares based on a time sequence of a node root certificate generated for each shareholder node.

* * * * *

UNITED STATES PATENT AND TRADEMARK OFFICE
CERTIFICATE OF CORRECTION

PATENT NO. : 10,722,649 B2
APPLICATION NO. : 16/722356
DATED : July 28, 2020
INVENTOR(S) : Qiang Tang Page 1 of 1

It is certified that error appears in the above-identified patent and that said Letters Patent is hereby corrected as shown below:

In the Claims

In Column 20, Line 59, Claim 1: delete "with a the blockchain;" and insert -- with the blockchain; --, therefor.

In Column 20, Line 62, Claim 1: delete "on the blockchain. and" and insert -- on the blockchain and --, therefor.

In Column 21, Line 52, Claim 7: delete "with a the blockchain;" and insert -- with the blockchain; --, therefor.

In Column 22, Line 54, Claim 13: delete "with a the blockchain;" and insert -- with the blockchain; --, therefor.

In Column 22, Line 57, Claim 13: delete "on the blockchain. and" and insert -- on the blockchain and --, therefor.

Signed and Sealed this
Thirteenth Day of September, 2022

Katherine Kelly Vidal
*Director of the United States Patent and Trademark Office*